(12) United States Patent
Locke et al.

(10) Patent No.: US 11,547,789 B2
(45) Date of Patent: Jan. 10, 2023

(54) OXYGEN THERAPY WITH FLUID REMOVAL

(71) Applicant: KCI Licensing, Inc., San Antonio, TX (US)

(72) Inventors: Christopher Brian Locke, Bournemouth (GB); Justin Alexander Long, Lago Vista, TX (US); Kristine M. Kieswetter, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 16/646,464

(22) PCT Filed: Aug. 21, 2018

(86) PCT No.: PCT/US2018/047248
§ 371 (c)(1),
(2) Date: Mar. 11, 2020

(87) PCT Pub. No.: WO2019/055176
PCT Pub. Date: Mar. 21, 2019

(65) Prior Publication Data
US 2020/0289806 A1 Sep. 17, 2020

Related U.S. Application Data

(60) Provisional application No. 62/558,435, filed on Sep. 14, 2017.

(51) Int. Cl.
*A61M 1/00* (2006.01)
*A61M 35/00* (2006.01)
*A61F 13/02* (2006.01)

(52) U.S. Cl.
CPC ........... *A61M 1/90* (2021.05); *A61F 13/0216* (2013.01); *A61F 13/0253* (2013.01); *A61M 1/74* (2021.05);
(Continued)

(58) Field of Classification Search
CPC .. A61M 1/0023; A61M 1/0088; A61M 35/30; A61M 1/0084; A61M 2202/0208;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Adam Marcetich
*Assistant Examiner* — Nhu Q. Tran

(57) ABSTRACT

An apparatus for treating a tissue site includes a dressing, an oxygen source, a valve, and a negative-pressure source. The dressing is configured to be sealed around the tissue site. The oxygen source is fluidly coupled to the dressing and configured to provide a low flow of oxygen. A first port of the valve is fluidly coupled to the dressing and the valve moves between a closed position preventing flow through the valve and an open position permitting flow through the valve. The negative-pressure source is fluidly coupled to a second port of the valve and provides negative pressure to the second port of the valve at a non-therapeutic level. The valve (Continued)

separates the negative-pressure source from the dressing and selectively opens when a positive pressure is applied on an upstream side of the valve.

18 Claims, 5 Drawing Sheets

(52) U.S. Cl.
CPC .............. *A61M 1/743* (2021.05); *A61M 1/85* (2021.05); *A61M 35/30* (2019.05); *A61M 2202/0208* (2013.01); *A61M 2205/3331* (2013.01)

(58) Field of Classification Search
CPC .............. A61M 1/0035; A61M 1/0031; A61M 2205/3331; A61F 13/00068; A61F 13/0216
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0118096 A1* | 5/2007 | Smith ............... A61B 5/445 604/541 |
| 2011/0106030 A1* | 5/2011 | Scholz ............ A61M 27/00 604/319 |
| 2011/0130712 A1* | 6/2011 | Topaz ............. A61F 13/00029 604/23 |
| 2012/0283626 A1* | 11/2012 | Belson ............ A61M 35/30 604/23 |
| 2013/0085462 A1* | 4/2013 | Nip ................. A61M 1/0058 604/315 |
| 2013/0110058 A1* | 5/2013 | Adie ............... A61M 1/74 604/319 |

(56) References Cited

U.S. PATENT DOCUMENTS

| | | | |
|---|---|---|---|
| 2013/0131616 A1 | 5/2013 | Locke | |
| 2013/0303975 A1* | 11/2013 | Gvodas, Jr. | A61M 1/94 604/23 |
| 2014/0163491 A1 | 6/2014 | Schuessler et al. | |
| 2015/0080788 A1 | 3/2015 | Blott et al. | |
| 2015/0119830 A1* | 4/2015 | Luckemeyer | A61F 13/00051 604/319 |
| 2016/0030722 A1* | 2/2016 | Anderson | A61M 1/0025 604/20 |
| 2016/0166781 A1* | 6/2016 | Sarangapani | A61M 1/0023 604/23 |
| 2020/0188563 A1* | 6/2020 | Robinson | A61F 13/00042 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2010147592 A1 | 12/2010 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, Pa, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, Md., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.

PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al.; "Effective Management of incisional and cutaneous fistulae with closed suction vound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and

(56) References Cited

OTHER PUBLICATIONS

Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion for Corresponding Application No. PCT/US2018/047248, dated Nov. 30, 2018.

\* cited by examiner

OXYGEN THERAPY WITH FLUID REMOVAL

RELATED APPLICATION

This application claims the benefit, under 35 USC 119(e), of the filing of U.S. Provisional Patent Application No. 62/558,435, entitled "OXYGEN THERAPY WITH FLUID REMOVAL," filed Sep. 14, 2017, which is incorporated herein by reference for all purposes.

TECHNICAL FIELD

The invention set forth in the appended claims relates generally to tissue treatment systems and more particularly, but without limitation, to oxygen therapy with fluid removal.

BACKGROUND

Clinical studies and practice have shown that the application of concentrated oxygen to a tissue site can be highly beneficial for new tissue growth or healing, particularly for chronic wounds. For example, hyperbaric oxygen therapy may be particularly beneficial for tissue with poor oxygenation, such as often seen in diabetic foot ulcers.

While the clinical benefits of oxygen therapy are widely known, improvements to therapy systems, components, and processes may benefit healthcare providers and patients.

BRIEF SUMMARY

New and useful systems, apparatuses, and methods for treating a tissue site are set forth in the appended claims. Illustrative embodiments are also provided to enable a person skilled in the art to make and use the claimed subject matter.

For example, in some embodiments, oxygen can be delivered continuously from a low-flow oxygen source to a dressing that can be applied to a tissue site. The dressing may include a high-sealing cover that can retain the oxygen, and a tissue interface that allows gas communication with the oxygen source. The cover may be made from silicone, hydrogel, or hydrocolloid, for example. The dressing may also include a filler in some embodiments, which can be hydrophilic to prevent edge strike-through, lifting of the cover, and periwound maceration. A low-level source of negative-pressure can also be fluidly coupled to the dressing, which can remove fluids without necessarily delivering therapeutic levels of negative-pressure to the dressing. An in-line check valve or regulating valve may be disposed in a fluid path between the source of negative-pressure and the dressing. A controller can monitor and regulate pressure at the distal end of the fluid path between the valve and the negative-pressure source such that a target pressure can be delivered to the valve. For example, a target pressure may be a range of −20 to −40 mmHg in some embodiments. A static column of fluid may form in the fluid path between the valve and the negative-pressure source, and the negative-pressure source may generate a pressure in a range of −70 to −120 mmHg to achieve the target pressure on the downstream side of the valve.

In some examples, the valve may be omitted and the negative-pressure source can be fluidly coupled to the dressing directly. The negative-pressure source may intermittently produce negative pressure to remove fluids. A target pressure of about −20 mmHg to about 30 mmHg may be suitable for such a configuration.

More generally, in some embodiments, an apparatus for treating a tissue site may include a dressing, an oxygen source, a valve, and a negative-pressure source. The dressing can be configured to be sealed around the tissue site, and the oxygen source can be fluidly coupled to the dressing and configured to provide a low flow of oxygen. A first port of the valve can be fluidly coupled to the dressing, and the valve can move between a closed position preventing flow through the valve and an open position permitting flow through the valve. The negative-pressure source may be fluidly coupled to a second port of the valve to provide negative pressure to the second port of the valve in an operating range of 15 millimeters of mercury to 50 millimeters of mercury. In some embodiments, the operating range may be 20 millimeters of mercury to 40 millimeters of mercury. The valve separates the negative-pressure source from the dressing and can selectively open when a positive pressure is applied on an upstream side of the valve or an increased negative-pressure is applied to the downstream side.

In some embodiments, the dressing may comprise a tissue interface and a cover. The cover may be disposed over, or configured to be disposed over, the tissue interface. A sealing layer may be disposed between the cover and the tissue interface in some examples. The dressing may also include a filler configured to be disposed between the cover and the tissue interface. A hydrophilic filler may be particularly suitable for preventing edge strike-through, lifting of the cover, and periwound maceration, for example.

A method for treating a tissue site is also described herein, wherein some example embodiments include fluidly coupling the tissue site to an oxygen source; fluidly coupling the tissue site to a negative-pressure source through a valve moving between a closed position preventing flow through the valve and an open position permitting flow through the valve; reducing pressure proximate to the tissue site to about −25 millimeters of mercury; delivering oxygen from the oxygen source to the tissue site; maintaining a negative pressure at a downstream side of the valve in a range of about 20 millimeters of mercury to about 40 millimeters of mercury; and selectively opening the valve when a positive pressure is applied to an upstream side of the valve.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
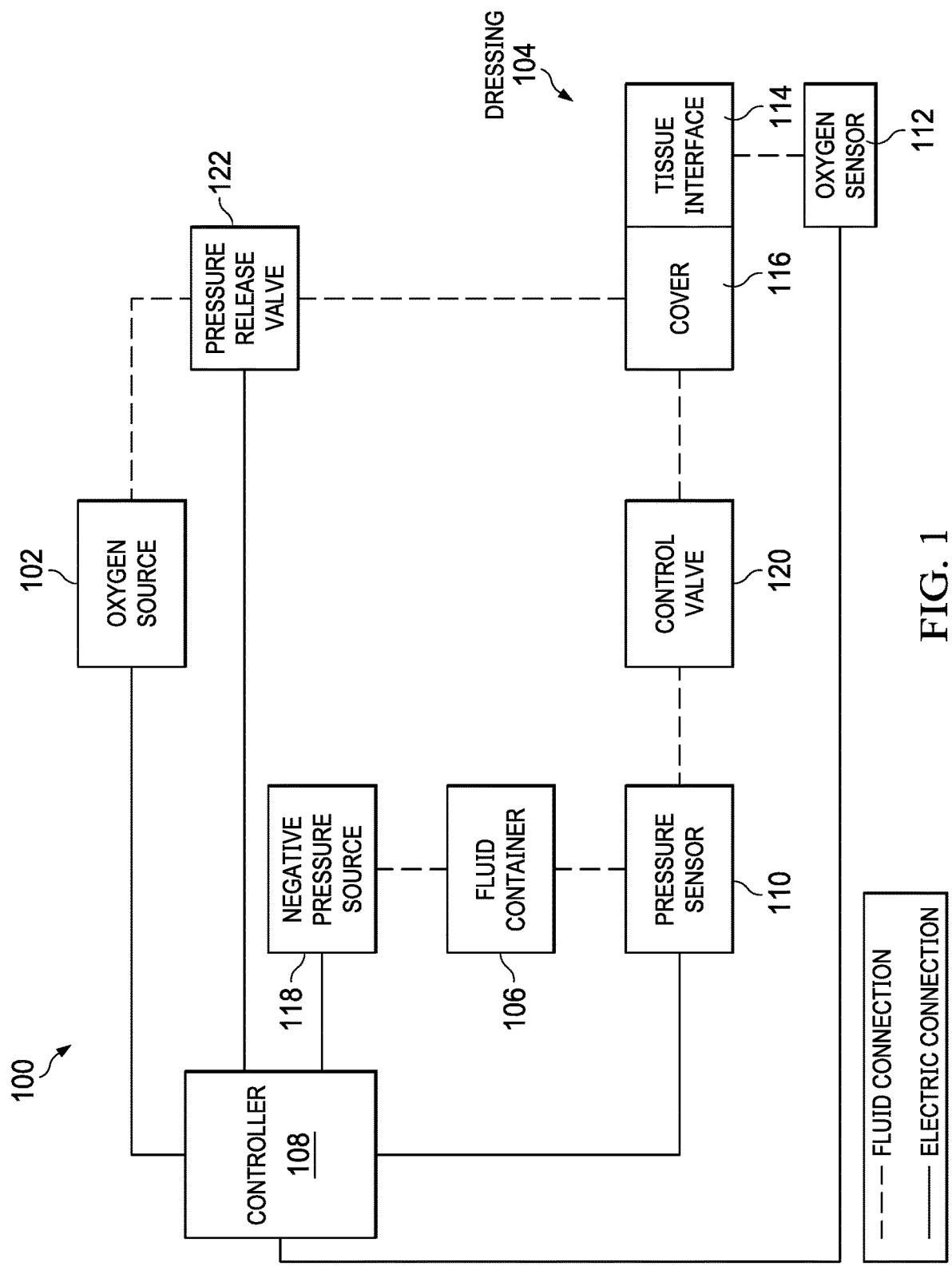
FIG. 1 is a functional block diagram of an example embodiment of the therapy system that can provide oxygen therapy with fluid removal in accordance with this specification.

FIG. 1 is a simplified functional block diagram of an example embodiment of a therapy system 100 that can provide oxygen therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, full-thickness burns, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue.

The therapy system 100 may include a source or supply of oxygen, such as an oxygen source 102, a dressing 104, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an oxygen sensor 112, or both, coupled to the controller 108. As illustrated in the example of FIG. 1, the dressing 104 may comprise or consist essentially of a tissue interface 114, a cover 116, or both in some embodiments.

The dressing 104 may also include a sealing layer. In some embodiments, the sealing layer may be disposed between the cover 116 and the tissue interface 114. The sealing layer may be coupled to or integral with the cover 116 or the tissue interface 114 in various embodiments. In some embodiments, the cover 116 may comprise or consist essentially of a sealing layer.

In some examples, the dressing 104 may also include a filler configured to be disposed between the cover 116 and the tissue interface 114. A hydrophilic filler may be particularly suitable for preventing edge strike-through, lifting of the cover, and periwound maceration, for example. Suitable hydrophilic fillers may include open-cell hydrophilic foams or super absorbent polymers in the form of particulates, fibers, or textiles, for example. In some embodiments, a hydrophilic filler may comprise or consist essentially of an assembly of super absorbent textile between two or more layers of non-woven textile.

The therapy system 100 may also include a source of negative pressure, such as a negative-pressure source 118. The negative-pressure source 118 may be fluidly coupled to the dressing 104, as illustrated in the example of FIG. 1. In the example of FIG. 1, the negative-pressure source 118 is fluidly coupled to the dressing 104 indirectly, through a container 106 and a control valve, such as a valve 120.

The valve 120 may comprise a first port and a second port, wherein the first port is fluidly coupled to the dressing 104 and the second port is fluidly coupled to the negative-pressure source 118. The valve 120 may be an in-line check valve or regulating valve, for example. The valve 120 can move between a first position and a second position to control flow through the valve 120. For example, the first position may be a closed position preventing flow through the valve 120, and the second position may be an open position permitting flow through the valve 120. The valve 120 may be actuated by a pressure differential between the first port and the second port. For example, in some embodiments, the valve 120 may be configured to remain closed against negative-pressure applied to the downstream side of the valve 120 and can be opened by low hyperbaric pressure on the upstream side of the valve 120. In some embodiments, the opening pressure may be adjustable either during manufacture or operation to optimize fluid removal. For example, some embodiments of the valve 120 may have fixed settings for high, medium, and low opening pressure.

In some embodiments, the therapy system 100 may further include a regulator, such as a pressure relief valve 122, which can vent oxygen under some conditions or operating parameters. For example, in some embodiments, the pressure relief valve 122 may be configured to vent oxygen at a pressure in excess of 30 to 40 millimeters of mercury (mmHg) positive pressure. The pressure relief valve 122 may not be required depending upon the nature of the oxygen generating source and the nature of the negative pressure device function.

Some components of the therapy system 100 may be housed within or used in conjunction with other components, such as sensors, processing units, alarm indicators, memory, databases, software, display devices, or user interfaces that further facilitate therapy. For example, in some embodiments, the oxygen source 102 may be combined with the negative-pressure source 118, the controller 108, and other components into a therapy unit.

In general, components of the therapy system 100 may be coupled directly or indirectly. For example, the negative-pressure source 118 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. In some embodiments, components may also be coupled by virtue of physical proximity, being integral to a single structure, or being formed from the same piece of material. For example, the oxygen source 102 and the negative-pressure source 118 may be electrically coupled to the controller 108. The oxygen source 102 may be fluidly coupled to one or more distribution components, which provide a fluid path to a tissue site.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSAT.R.A.C.™ Pad available from KCI of San Antonio, Tex.

An oxygen supply, such as the oxygen source 102, may be a reservoir of concentrated oxygen at a positive pressure, or may be a reservoir of oxygen coupled to a manual or electrically-powered device, such as a pump or a micropump, for example. In some embodiments, the oxygen source 102 may be a low-flow oxygen system, which can provide a continuous flow of oxygen at a rate of less than or equal to 25 milliliters per hour (ml/hr) continuously. A rate not greater than 20 ml/hr or 15 ml/hr and not less than 3 ml/hr may be particularly suitable for many applications. Examples of suitable low-flow oxygen systems are the TransCu O2® oxygen concentrator from EO2, the NATROX generator from Inotec AMD, and EpiFlo from Ogenix.

A controller, such as the controller 108, may be a microprocessor or computer programmed to operate one or more components of the therapy system 100, such as the oxygen source 102 and/or the negative-pressure source 118. In alternative embodiments, each of the oxygen source 102 and the negative-pressure source 118 may include independent controllers, which can control the functions for the oxygen source 102 and the negative-pressure source 118 independently. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 118, the pressure generated by the negative-pressure source 118, or the pressure distributed to the control valve 120, for example. Other example operating parameters may include the power applied to the oxygen source 102, the pressure of oxygen from the oxygen source 102, oxygen concentration, and/or control of the pressure relief valve 122 in some embodiments. The controller 108 is also preferably configured to receive one or more input signals, such as a feedback signal, and programmed to modify one or more operating parameters based on the input signals.

Sensors, such as the pressure sensor 110 or the oxygen sensor 112 are generally known in the art as any apparatus operable to detect or measure a physical phenomenon or property, and generally provide a signal indicative of the phenomenon or property that is detected or measured. For example, the pressure sensor 110 and the oxygen sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezoresistive strain gauge. The oxygen sensor 112 may optionally measure the quantity of oxygen or saturation of oxygen supplied from the oxygen source 102 in some embodiments. Preferably, the signals from such sensors are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 may be generally adapted to contact a tissue site. The tissue interface 114 may be partially or fully in contact with a tissue site. If a tissue site is a wound, for example, the tissue interface 114 may partially or completely fill the wound, or may be placed over the wound. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Moreover, any or all of the surfaces of the tissue interface 114 may have projections or an uneven, course, or jagged profile that can induce strains and stresses on a tissue site, which can promote granulation at the tissue site.

In some embodiments, the tissue interface 114 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, a manifold may also be adapted to receive oxygen from an oxygen source and distribute the oxygen through multiple apertures across a tissue site. In other embodiments, the fluid path may be reversed or a secondary fluid path may be provided to facilitate delivering fluid across a tissue site. In additional or alternative embodiments, the pathways of a manifold may be interconnected to improve distribution or collection of fluids across a tissue site. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 114 may be a foam having pore sizes in a range of 400-600 microns. The tensile strength of the tissue interface 114 may also vary according to needs of a prescribed therapy. For example, the tensile strength of a foam may be increased for instillation of topical treatment solutions. In one non-limiting example, the tissue interface 114 may be an open-cell, reticulated polyurethane foam such as GRANUFOAM™ dressing or V.A.C. VERAFLO™ dressing, both available from KCI of San Antonio, Tex.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic foam is a polyvinyl alcohol, open-cell foam such as V.A.C. WHITEFOAM™ or polyurethane ester VERAFLO dressings available from KCI of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 114 may be constructed from bioresorbable or biologically-based materials. Suitable materials may include, without limitation, a polymeric blend of polylactic acid (PLA) and polyglycolic acid (PGA). The polymeric blend may also include without limitation polycarbonates, polyfumarates, and capralactones. Other suitable materials may include dextran, hyaluronic acid, keratins, silks, carboxymethylcellulose, collagen, adipose tissue, or dermal tissue, for example. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include dextran, keratin, silks, calcium phosphate, collagen, PLA/PGA, coral hydroxyapatites, carbonates, or processed allograft materials.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to retain oxygen under the cover 116. For example, the cover 116 may be configured to provide a seal with a leak rate no greater than approximately 5 milliliters per hour. In some embodiments, the cover 116 may also have a high moisture-vapor transmission rate (MVTR). For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired pressure from the oxygen supply source can be maintained. In some embodiments, the cover 116 may further include indicators which change color in the present of therapeutic levels of oxygen in the wound.

The sealing layer may be a soft, pliable material suitable for providing a fluid seal with a tissue site. For example, the sealing layer may comprise or consist essentially of a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, hydrogenated styrenic copolymers, acrylic adhesives, light sensitive or light-deactivated adhesives, or any combination of these materials. In some embodiments, the sealing layer may have a thickness between about 500 microns (μm) and about 1000 microns (μm). In some embodiments, the sealing layer may have a stiffness between about 5 Shore OO and about 80 Shore OO. Further, the sealing layer may be comprised of hydrophobic or hydrophilic materials.

In some embodiments, the sealing layer may be a hydrophobic-coated material. For example, the sealing layer may be formed by coating a spaced material, such as, for example, woven, nonwoven, molded, or extruded mesh with a hydrophobic material. The hydrophobic material for the coating may be a soft silicone, for example. The sealing layer may have apertures in some embodiments.

An attachment device may be used to attach the cover 116 to an attachment surface, such as undamaged epidermis, a gasket, or another cover. An attachment device may take many forms. For example, an attachment device may be a medically-acceptable, pressure-sensitive adhesive that extends about a periphery, a portion, or an entire cover. In some embodiments, for example, some or all of the cover 116 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel. In some embodiments, an attachment device may be disposed between the cover 116 and a perforated sealing layer, through which the attachment device may bond the cover 116 to an attachment surface.

A negative-pressure supply, such as the negative-pressure source 118, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 118 may vary, the pressure is generally a low vacuum, also commonly referred to as a rough vacuum, between −5 mm Hg (−667 Pa) and −500 mm Hg (−66.7 kPa). Therapeutic ranges between −50 mm Hg (−6.7 kPa) and −125 mm Hg (−16.0 kPa) may be particularly suitable for some applications.

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

Figure 2:
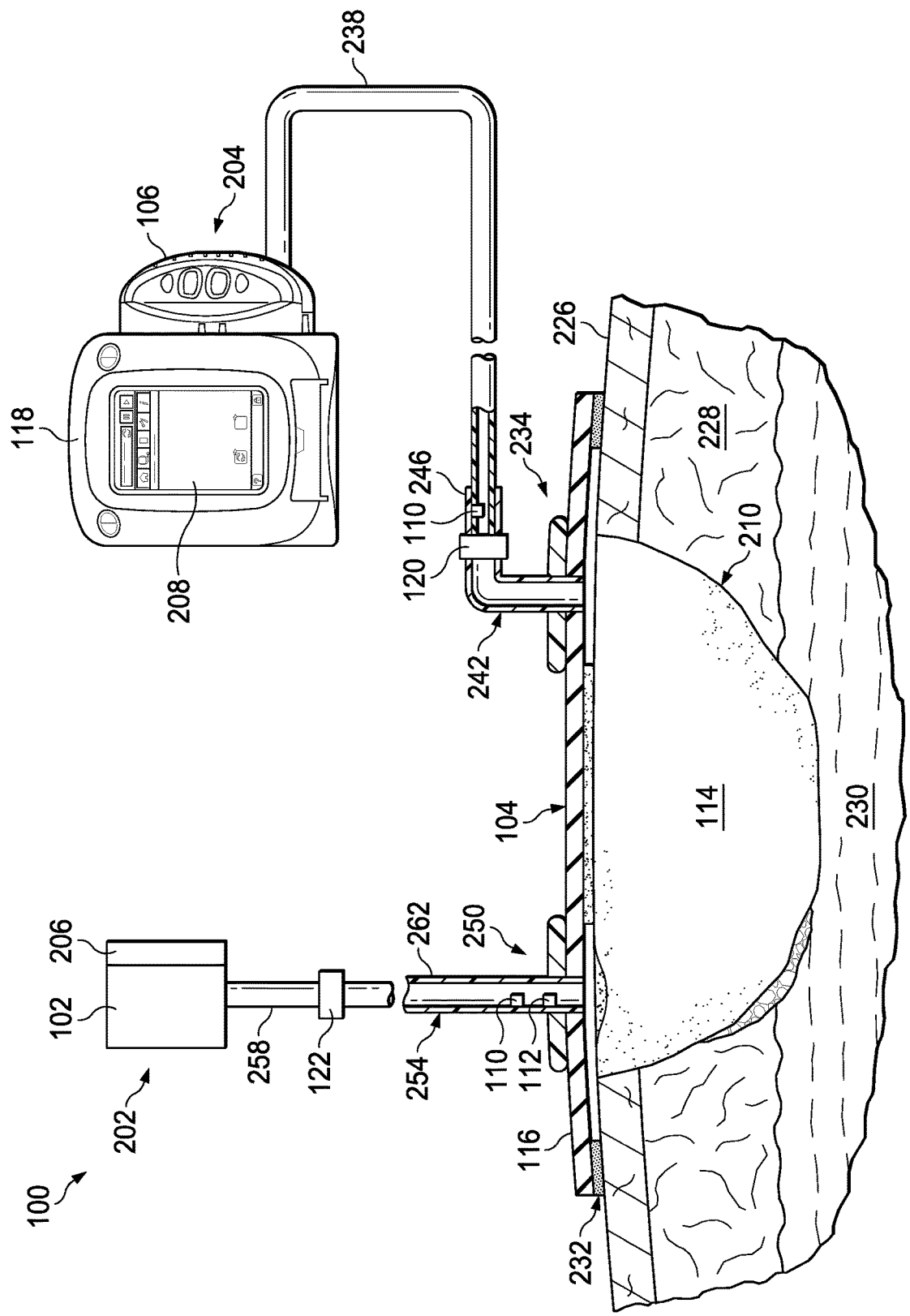
FIG. 2 is a schematic diagram of an example embodiment of the therapy system of FIG. 1.

FIG. 2 is a schematic diagram of an example of the therapy system 100, illustrating additional details that may be associated with some embodiments. As illustrated in the example of FIG. 2, some embodiments of the therapy system 100 the oxygen source 102 may be associated with an oxygen unit 202 and the negative-pressure source 118 may be associated with a negative-pressure unit 204. FIG. 2 also illustrates an example in which the oxygen source 102 and the negative-pressure source may be independently controlled. For example, the oxygen source 102 may be controlled by an oxygen controller 206 associated with the oxygen unit 202, and the negative-pressure source 118 may be controlled by a negative-pressure controller 208 associated with the negative-pressure unit 204.

In the example of FIG. 2, the therapy system 100 may provide a first dressing interface 234 and a second dressing interface 250. The first dressing interface 234 may facilitate coupling the negative-pressure unit 204 to the dressing 104. For example, the first dressing interface 234 may include a negative-pressure interface 242, which may include a straight port and/or an elbow port, such as elbow port 246 that may be fluidly coupled to a fluid conductor 238. In this illustrative, non-limiting embodiment, the elbow port 246 extends through the cover 116 to the tissue interface 114, but numerous arrangements are possible. In some embodiments, the negative-pressure interface 242 may include a hydrophobic filter in some embodiments.

The second dressing interface 250 may facilitate coupling of the oxygen unit 202 to the dressing 104. In some embodiments, the oxygen source 102 may be fluidly coupled to the tissue interface 114 through a fluid conductor 258 to a fluid-delivery interface 254, which may include a straight port and/or an elbow port, such as straight port 262. The fluid-delivery interface 254 may be fluidly coupled to the dressing 104 and may pass through a hole cut in the cover 116, for example. The hole cut in the cover 116 for the fluid-delivery interface 254 may be separated from the location of elbow port 246. The fluid-delivery interface 254 may allow for a fluid, such as concentrated oxygen, to be delivered by the therapy system 100 through the cover 116 and to the tissue interface 114. In some embodiments, the fluid-delivery interface 254 may include an inlet pad. The inlet pad may be a material that is not absorbent. In some embodiments, the inlet pad may be an elastomer. For example, the inlet pad may be an elastic polymer, such as polyurethane, thermoplastic elastomers, polyether block amide (PEBAX), polyisoprene, polychloroprene, chlorosulphonated polythene, and polyisobutylene, blends and copolymers. In one illustrative embodiment, the fluid-delivery interface 254 and the negative-pressure interface 242 may be integrated into a single pad for the delivery and removal of fluids. In some embodiments, the fluid-delivery interface 254 may include a hydrophobic filter in some embodiments.

In the example of FIG. 2, the tissue interface 114 is placed within, over, on, or otherwise proximate to a tissue site, such as a wound 210. The wound 210 in the example of FIG. 2 penetrates an epidermis 226 and a dermis 228 into subcutaneous tissue 230. The cover 116 may be placed over the tissue interface 114 and sealed to an attachment surface near the wound 210 by an attachment device 232. For example, the cover 116 may be sealed to intact epidermis 226 peripheral to the wound 210. Thus, the dressing 104 can provide a sealed therapeutic environment proximate to the wound 210, substantially isolated from the external environment.

In some embodiments, oxygen may be delivered continuously to the dressing 104 from oxygen source 102 through the fluid conductor 258 and the fluid-delivery interface 254 attached to the cover 116. The fluid mechanics of using pressure to move fluids through a fluid conductor can be mathematically complex. However, the basic principles of fluid mechanics applicable to oxygen therapy are generally well-known to those skilled in the art, and the movement of oxygen from the oxygen source 102 may be described illustratively herein as "delivering," "distributing," or "generating" oxygen, for example.

In general, fluids flow toward lower pressure along a fluid path. Thus, the term "downstream" typically implies something in a fluid path relatively further away from a source of positive pressure or closer to a source of negative pressure. Conversely, the term "upstream" implies something relatively closer to a source of positive pressure or further away from a source of negative pressure. Similarly, it may be convenient to describe certain features in terms of fluid "inlet" or "outlet" in such a frame of reference. This orientation is generally presumed for purposes of describing various features and components herein.

The percentage or concentration of oxygen within the wound 210 can increase to levels of at least 80% over time, improving the pO2 levels in the wound tissue. The dressing 104 is designed such that it can manage some buildup of internal pressure. For example, the oxygen unit 202 may have a back-pressure sensing system, which may shut down the flow of oxygen or reduce the low oxygen flow pressure at the wound 210 exceeds a safety threshold.

As illustrated in the example of FIG. 2, the valve 120 may be positioned between the negative-pressure interface 242 and the negative-pressure source 118. It may be particularly advantageous to place the valve 120 closer to the negative-pressure interface 242 than the negative-pressure source 118. More than one valve 120 may be disposed in the fluid path between the negative-pressure interface 242 and the negative-pressure source 118 to encourage fluid movement and prevent backflow. In some embodiments, the negative-pressure source 118 may provide a continuous negative pressure on the valve 120. The pressure on the valve 120 may be affected by head-pressure drop and the length of the fluid conductor 238, for example. In some embodiments, the negative-pressure unit 204 may compensate for these types of effects. For example, in some embodiments it may be desired to apply negative pressure in a target range of −20 mmHg to −40 mmHg to the valve 120, and the negative-pressure unit 204 may increase the pressure generated to −70 mmHg to −120 mmHg to achieve a pressure within the target range at the valve 120.

In operation, the negative-pressure source 118 may apply non-therapeutic levels of negative pressure to initially reduce the pressure in the dressing. For example, non-therapeutic levels may include a range of about 0 mmHg to about −50 mmHg in some embodiments, and the initial pressure in the dressing 104 may be about −25 mmHg. The negative-pressure source 118 may subsequently maintain a level of negative pressure at the second port of the valve 120 in a non-therapeutic operating range. In some embodiments, an operating range of about −15 mmHg to about −50 mmHg may be suitable. Fluid may be exuded from the wound 210 into the dressing 104. If the volume of exudate and oxygen exceeds the volume of the dressing 104, the pressure in the dressing 104 may increase and atmospheric pressure against the dressing 104 can push the exudate up the negative-pressure interface 242 and against the valve 120. The valve 120 can be opened if the pressure difference between the upstream side of the valve 120 and the downstream side of the valve 120 exceeds the opening pressure of the valve 120. For example, the increase in pressure from exudate and oxygen on the upstream side of the valve 120 can open the valve 120, allowing the gas and fluids through and into the fluid conductor 238. The pressure differential can also be increased by increasing the negative pressure applied to the downstream side of the valve 120, which can also open the valve 120 in some examples. The negative pressure on the downstream side of the valve 120 can advance the fluids through the fluid conductor 238 to the container 106.

Figure 3:
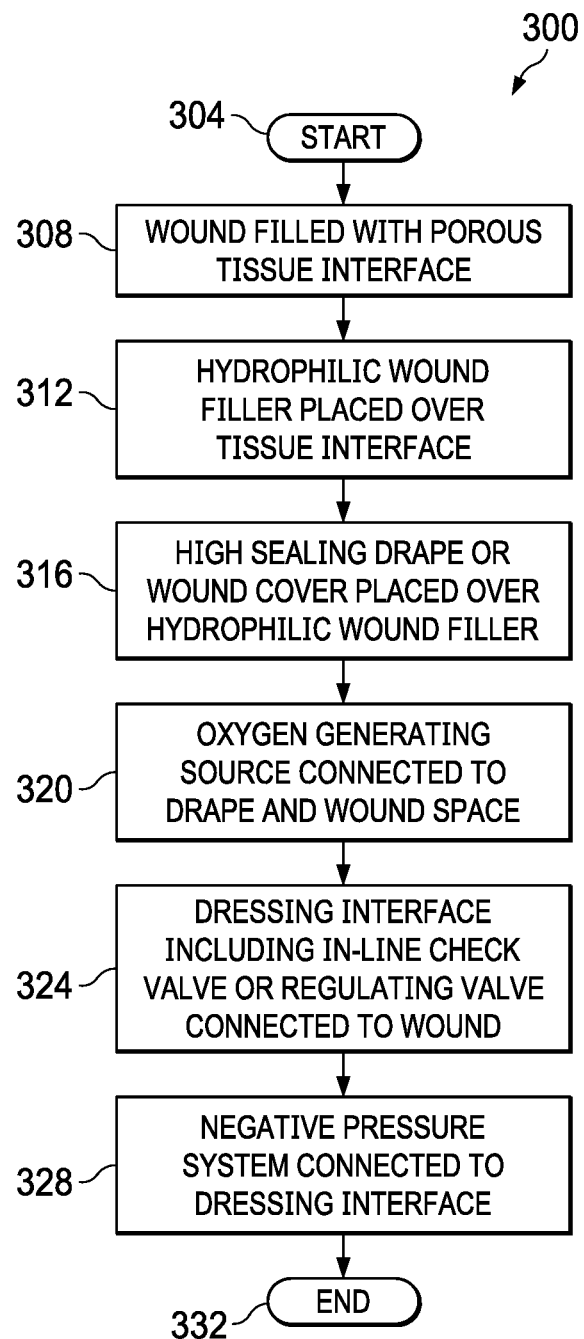
FIG. 3 is a flow chart illustrating an embodiment of a method for installing a therapy system which provides continuous oxygen and negative pressure treatment solutions to a dressing at a tissue site.

FIG. 3 is a flow chart illustrating a method 300 of installing the therapy system 100 at a tissue site, such as the wound 210. In the example embodiment of FIG. 3, the method 300 starts at 304. At 308, the wound 210 can be filled with the tissue interface 114. At 312, a filler may be placed over the tissue interface 114 in some embodiments. The filler may be hydrophilic in order to prevent edge strike-through, lifting of the cover 116, and peri-wound maceration. The filler may also be a foam material in some embodiments. In some embodiments, the filler may be combined with the tissue interface 114.

At 316, the cover, 116 may be placed over the tissue interface 114. The cover 116 may include indicators that can change color in the presence of therapeutic levels of oxygen in the wound 210. For example, such therapeutic levels may be at least 60 percent (%) and, more preferably, at least 80 percent (%). At 320, the oxygen source 102 can be connected to the tissue interface 114 through the cover 116. For example, fluid conductor 258 may mechanically and fluidly couple the oxygen source 102 to the fluid-delivery interface 254 in the dressing 104. The fluid-delivery interface 254 may be fluidly coupled to the dressing 104 and may pass through a hole cut in the cover 116. The fluid-delivery interface 254 may allow for a fluid, such as concentrated oxygen, to be delivered by the therapy system 100 through the cover 116 and to the tissue interface 114. At 324, the negative-pressure interface 242, including the valve 120 can be connected to the dressing 104. At 328, the negative-pressure source 118 can be connected to the negative-pressure interface 242 through the fluid conductor 238 to fluidly couple the negative-pressure source 118 to the tissue interface 114. The method 300 ends at 332.

Figure 4:
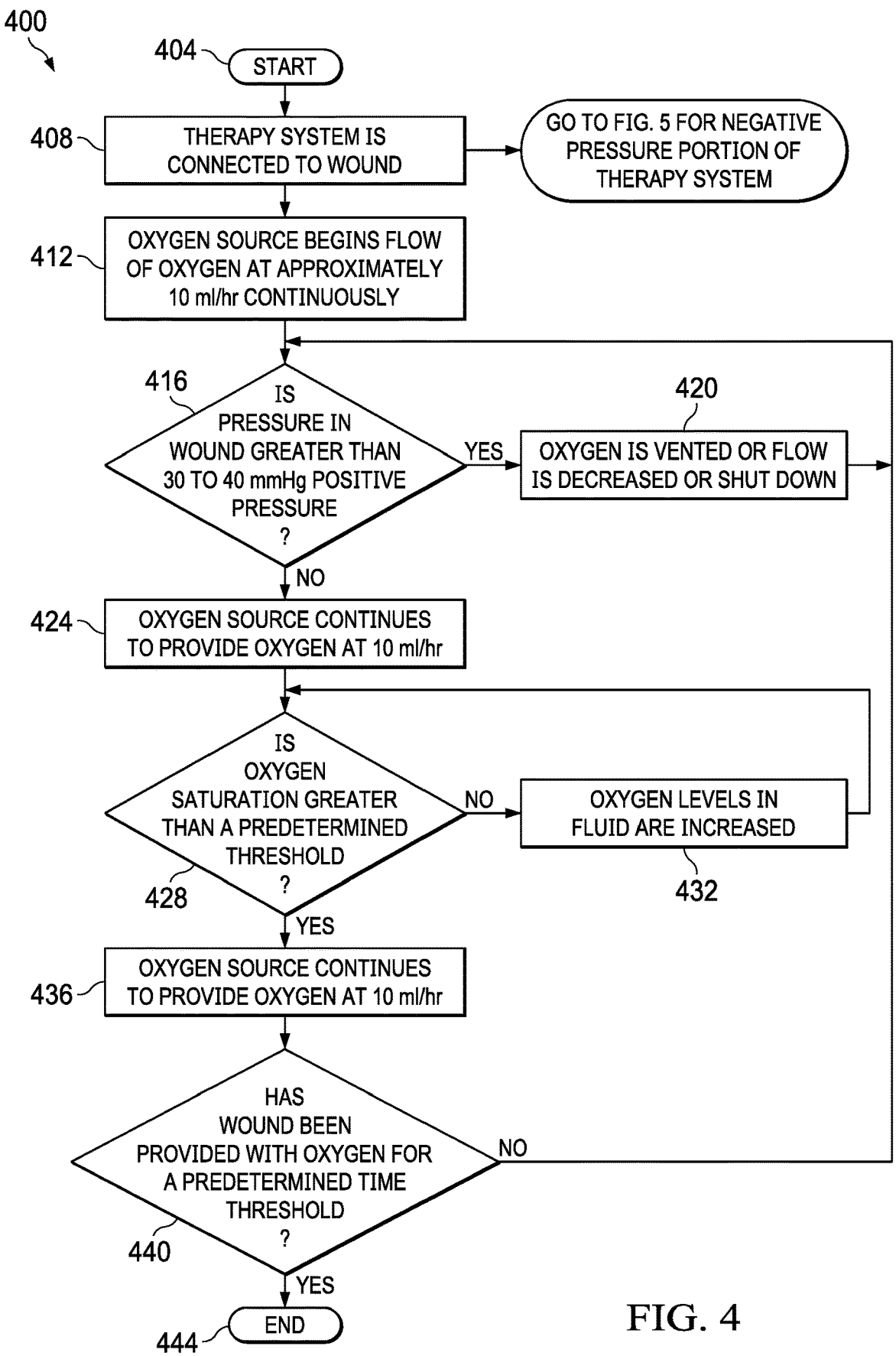
FIG. 4 is a flow chart illustrating an embodiment of a method for an oxygen supply portion of the therapy method for providing continuous oxygen and negative pressure treatment solutions to a dressing at a tissue site.

FIG. 4 is a flow chart illustrating an example method 400 of using the therapy system 100. In the example embodiment of FIG. 4, the method 400 starts at 404. At 408, the therapy system 100 is connected to the wound 210. For example, the therapy system 100 may be applied to the wound 210 by following the previously-described method 300 (FIG. 3). Once the therapy system 100 is connected to the wound 210, the oxygen source 102 and negative-pressure source 118 can be powered on. The remainder of the method 400 in FIG. 4 describes the use of an oxygen unit, such as the oxygen unit 202 of FIG. 2. The continuation of method 400 in FIG. 5 describes a method 500 for the use of a negative-pressure unit, such as the negative-pressure unit 204 of FIG. 2.

At 412, the oxygen source 102 can begin supplying oxygen. In some embodiments, the oxygen source 102 can be configured to provide oxygen at a rate of less than or equal to 20 ml/hr continuously. Preferably, the oxygen source 102 provides continuous flow of oxygen at a rate not greater than 15 ml/hr continuously, and, more preferably, at a rate of approximately 10 ml/hr continuously.

At 416, the method 400 may determine whether a pressure in the wound 210 is greater than a predetermined pressure threshold. For example only, the predetermined pressure threshold may be approximately 30 to 40 mmHg positive pressure. The dressing 104 may be configured such that it can manage some buildup of internal pressure in some embodiments. The predetermined pressure threshold may be set at a positive pressure corresponding to a threshold pressure over which the dressing 104 may release from the wound 210 (incorporating factors of safety). If the pressure in the wound 210 is greater than the predetermined pressure threshold, the pressure from the oxygen flow can be vented, released, or otherwise removed from the system at 420. For example, the dressing 104 or the fluid conductor 258 may include the pressure relief valve 122, which can vent oxygen at a pressure in excess of the predetermined pressure threshold. In other examples, the oxygen source 102 may have a back-pressure sensing system that can shut down the flow of oxygen or reduce the low oxygen flow during a sensed increased pressure at the wound 210.

If the pressure in the wound 210 is not greater than the predetermined pressure threshold, the oxygen source 102 continues to provide oxygen at 424.

At 428, the method 400 can determine whether the oxygen saturation is greater than a predetermined saturation threshold. For example, the predetermined saturation threshold may be within a range of approximately 50%-80%, and more preferably the predetermined saturation threshold may be approximately 60%. The therapy system 100 can be configured to provide a concentration of oxygen at high levels of >80% over time in some embodiments, which can improve the pO2 levels in the wound 210. If the oxygen saturation is not greater than the predetermined saturation threshold, the oxygen levels provided from the oxygen source 102 can be increased at 432.

If the oxygen saturation is greater than the predetermined saturation threshold at 428, the oxygen source 102 can continue to provide oxygen at 436.

At 440, the method 400 can determine whether the wound 210 has been provided with oxygen for a predetermined time threshold. The predetermined time threshold may be set by a doctor or other medical professional, for example, and may be based on the type, size, or severity of the wound 210, or some combination of the type, size, and severity. For example only, the predetermined time threshold may be within a range of 5 minutes to 72 hours or longer. If the wound 210 has not been provided with the oxygen for the predetermined time threshold at 440, the method 400 returns to 416 to determine whether the pressure in the wound 210 is greater than the predetermined pressure threshold.

If the wound 210 has been provided with the oxygen for the predetermined time threshold at 440, the method 400 ends at 444 and the oxygen source 102 can be powered down.

Figure 5:
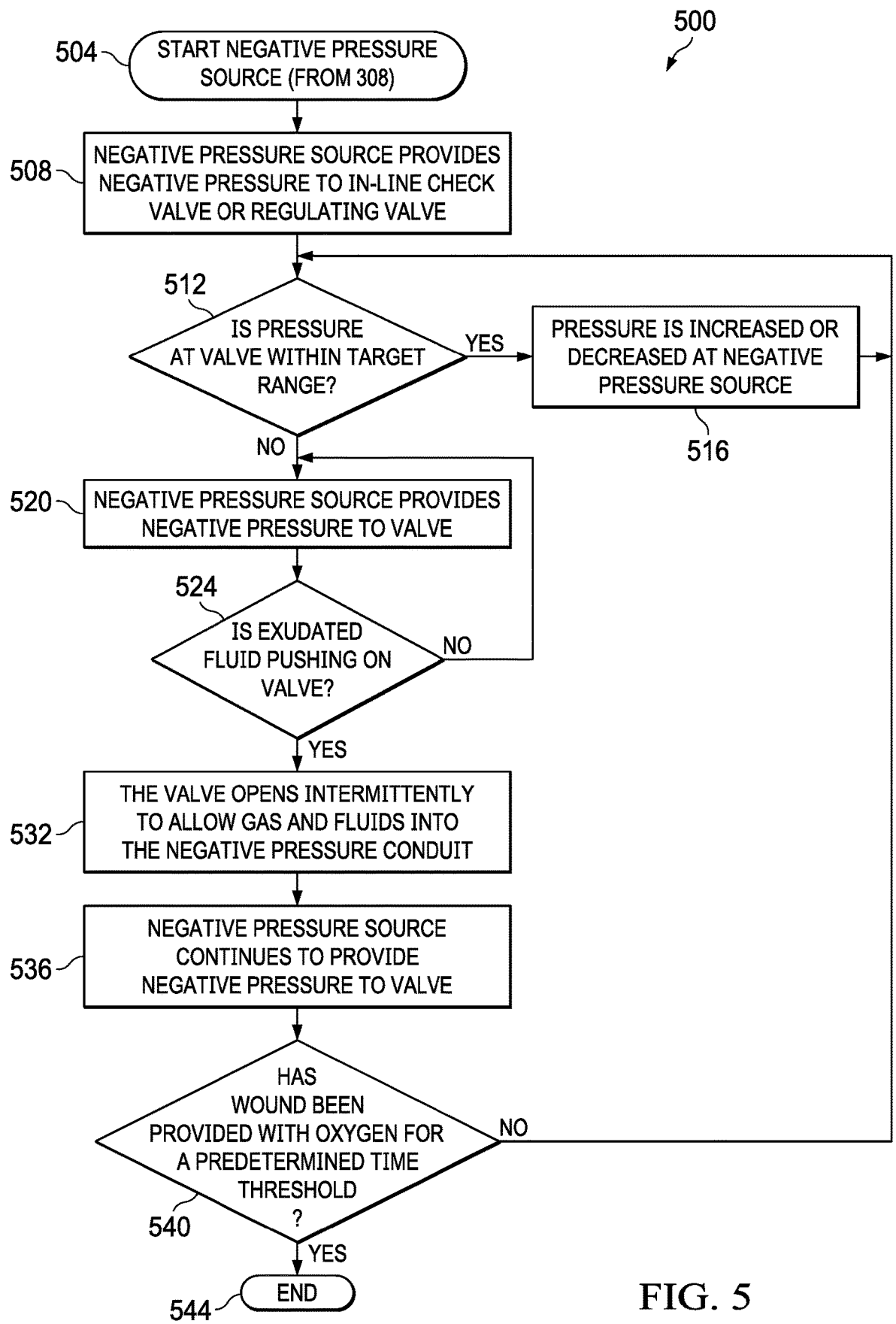
FIG. 5 is a flow chart illustrating an embodiment of a method for a negative pressure portion of the therapy method for providing continuous oxygen and negative pressure treatment solutions to a dressing at a tissue site.

At 408, after the therapy system 100 is connected to the wound 210, both the oxygen source 102 and the negative-pressure source 118 can be powered on. Referring to FIG. 5, the method 500 for using the negative-pressure unit 204 is illustrated.

Method 500 starts at 504. At 508, the negative-pressure source 118 can begin providing negative pressure. The valve 120 may be positioned between the negative-pressure interface 242 and the container 106 for regulating the negative pressure supplied to the wound 210. The negative-pressure source 118 can creates a continuous negative pressure on the valve 120 in some examples. In some embodiments, the negative-pressure delivered to the valve 120 can be affected by the head-pressure drop and length of the fluid path between the negative-pressure source 118 and the valve 120. If the dressing 104 is well sealed, a static column of fluid may form in the fluid path between the valve 120 and the negative-pressure source 118, and the output of the negative-pressure source 118 may be increased to compensate in some embodiments. For example, the pump pressure delivered to the container 106 may be increased by −70 mmHg to −120 mmHg to achieve a non-therapeutic pressure at the valve 120 within a target range of about −20 mmHg to −40 mmHg in some embodiments.

At 512, the method 500 determines whether the pressure is within the target range at the valve 120. In some embodiments, for example, the pressure sensor 110 may be positioned near the valve 120 to determine the pressure at the valve 120. If the pressure is not within the target range at 512, the output of the negative-pressure source 118 can be increased or decreased at 516. The method 500 can then re-check the pressure at the valve 120 at 512.

If the pressure is within the target range at 512, the negative-pressure source 118 can continue to provide low-level negative pressure to the valve 120 at 420. For example only, the negative pressure may continue to be supplied such that the pressure delivered to the valve 120 is in the range of −20 mmHg to −40 mmHg.

At 524, the method 500 determines whether exuded fluid is pushing on the valve 120. The valve 120 can be configured to have an opening pressure that is very finely balanced such that exuded fluid pushing on the valve 120 is the force that opens the valve 120. In operation, if the volume of exuded fluid and oxygen in the wound 210 fills the wound 210, the exuded fluid will be forced by atmospheric pressure to push against the cover 116, travel up the negative-pressure interface 242 to the valve 120. The valve 120 can open intermittently, as a result of the pressure from the exuded fluid, to allow the fluids through and into the fluid conductor 238. The negative pressure in the fluid conductor 238 can advance the fluids to the container 106 for storage.

If exuded fluid is not pushing on the valve 120 at 524, the valve 120 can remain closed and the negative-pressure source 118 can continue to provide low-level negative pressure at 528. For example only, the negative pressure may continue to be supplied such that the pressure delivered to the valve 120 is in the range of −20 mmHg to −40 mmHg. The method 500 can re-check if exuded fluid is pushing on the valve 120 at 524.

At 540, the method 500 determines whether the wound 210 has been provided with oxygen for a predetermined time threshold. The predetermined time threshold may be set by a doctor or other medical professional, for example, and may be based on the type and severity of the wound 210. For example only, the predetermined time threshold may be within a range of 5 minutes to 72 hours or longer. If the wound 210 has not been provided with oxygen for the predetermined time threshold at 540, the method 500 returns to 512 to determine whether the pressure at the valve 120 is within the target range.

If the wound 210 has been provided with the oxygen for the predetermined time threshold at 540, the method 500 ends at 544 and the negative-pressure source 118 is powered down.

The systems, apparatuses, and methods described herein may provide significant advantages. For example, some embodiments of the therapy system 100 may provide a continuous supply of oxygen to a tissue site, while also removing excess quantities of fluids once a dressing has been satiated, which may be advantageous for acute wounds with relatively larger volumes of exudate. The therapy system 100 can also increase the levels of oxygen within a tissue site to greater than 80% over time, improving the pO2 levels in the tissue in some examples. The therapy system 100 can also actively remove naturally-exuded fluid without absorbent dressings, which can be particularly advantageous for medium to high exuding wounds such as large VLU's or acute wounds.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. The words "preferred" and "preferably" refer to features or embodiments that can afford certain benefits, under certain circumstances. However, other features or embodiments may also be preferred, under the same or other circumstances. Furthermore, the recitation of one or more preferred embodiments does not imply that other embodiments are not useful and is not intended to exclude other embodiments from the scope of the claimed subject matter.

Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for treating a tissue site, the apparatus comprising:
    a dressing configured to be sealed around the tissue site;
    an oxygen source fluidly coupled to the dressing and configured to provide a low flow of oxygen;
    a first valve comprising a first port and a second port, wherein the first port is fluidly coupled to the dressing and the first valve moves between a closed position preventing flow through the first valve and an open position permitting flow through the first valve; and
    a negative-pressure source fluidly coupled to the second port of the first valve and providing negative pressure to the second port of the first valve in an operating range of non-therapeutic negative pressure;
    wherein the first valve selectively opens if a pressure differential between the first port and the second port is equal to or greater than an opening pressure of the first valve;
    a second valve fluidly coupled between the dressing and the oxygen source and configured to release excess pressure in the dressing.

2. The apparatus of claim 1, wherein the oxygen source provides a continuous flow of oxygen at a rate not greater than 25 milliliters per hour.

3. The apparatus of claim 1, wherein the oxygen source provides a continuous flow of oxygen at a rate not less than 3 milliliters per hour and not greater than 25 milliliters per hour.

4. The apparatus of claim 1, wherein the operating range of non-therapeutic negative pressure is from 15 millimeters of mercury to 50 millimeters of mercury.

5. The apparatus of claim 1, wherein a positive pressure is applied on an upstream side of the first valve.

6. The apparatus of claim 1, wherein the opening pressure of the first valve is at least 20 millimeters of mercury.

7. The apparatus of claim 1, further comprising a container disposed in a fluid path between the first valve and the negative-pressure source.

8. The apparatus of claim 1, wherein the dressing comprises a cover configured to have a leak rate no greater than 5 milliliters per hour.

9. The apparatus of claim 1, further comprising:
a pressure sensor fluidly coupled to the first valve; and
a controller operatively coupled to the negative-pressure source and to the pressure sensor, the controller configured to operate the negative-pressure source to maintain the negative pressure in the operating range based on a feedback signal from the pressure sensor.

10. The apparatus of claim 1, wherein the second valve is configured to release pressure in excess of 30 millimeters of mercury.

11. The apparatus of claim 1, wherein the dressing comprises:
a tissue interface; and
a cover configured to be disposed over the tissue interface.

12. The apparatus of claim 11, further comprising a sealing layer disposed between the cover and the tissue interface.

13. The apparatus of claim 12, wherein the sealing layer comprises a material or combination of materials selected from a group consisting of: a silicone gel, a soft silicone, hydrocolloid, hydrogel, polyurethane gel, polyolefin gel, hydrogenated styrenic copolymer gel, a foamed gel, a soft closed cell foam, polyurethane, polyolefin, hydrogenated styrenic copolymers, acrylic adhesives, and light-sensitive or light-deactivated adhesives.

14. The apparatus of claim 1, wherein the dressing comprises:
a tissue interface;
a hydrophilic filler configured to be disposed over the tissue interface; and
a cover configured to be disposed over the tissue interface.

15. The apparatus of claim 14, wherein the hydrophilic filler comprises a material selected from a group consisting of open-cell hydrophilic foams and super-absorbent polymers in a form of particulates, fibers, or textiles.

16. The apparatus of claim 14, wherein the hydrophilic filler comprises an assembly of super absorbent textile between two or more layers of non-woven textile.

17. The apparatus of claim 14, further comprising a sealing layer disposed between the cover and the hydrophilic filler.

18. The apparatus of claim 17, wherein the sealing layer comprises a material or combination of materials selected from a group consisting of: a silicone gel, a soft silicone, hydrocolloid, hydrogel, polyurethane gel, polyolefin gel, hydrogenated styrenic copolymer gel, a foamed gel, a soft closed cell foam, polyurethane, polyolefin, hydrogenated styrenic copolymers, acrylic adhesives, and light-sensitive or light-deactivated adhesives.

* * * * *